(12) United States Patent
Garcia et al.

(10) Patent No.: US 8,688,240 B1
(45) Date of Patent: Apr. 1, 2014

(54) DEVICE FOR NEURO-PHYSIOLOGIC STIMULATION

(71) Applicants: Julio Luis Garcia, Coral Gables, FL (US); Oresteban Carabeo, Miami Gardens, FL (US); Ruben Valdes, Beverly Hills, FL (US); Robert Valdes, Miami Lakes, FL (US)

(72) Inventors: Julio Luis Garcia, Coral Gables, FL (US); Oresteban Carabeo, Miami Gardens, FL (US); Ruben Valdes, Beverly Hills, FL (US); Robert Valdes, Miami Lakes, FL (US)

(73) Assignee: Mitosis Inc., Sunrise, FL (US)

( * ) Notice: Subject to any disclaimer, the term of this patent is extended or adjusted under 35 U.S.C. 154(b) by 0 days.

(21) Appl. No.: 13/675,287

(22) Filed: Nov. 13, 2012

Related U.S. Application Data

(63) Continuation-in-part of application No. 13/663,658, filed on Oct. 30, 2012, now Pat. No. 8,457,745.

(51) Int. Cl.
*A61N 1/32* (2006.01)

(52) U.S. Cl.
USPC .......................................... 607/145; 607/46

(58) Field of Classification Search
CPC . A61N 1/0553; A61N 1/3605; A61N 1/3603; A61N 1/36067; A61N 1/36071; A61N 1/36057

USPC ................ 607/40, 136, 133, 145–150, 2, 116
See application file for complete search history.

(56) References Cited

U.S. PATENT DOCUMENTS

| 4,165,750 A | 8/1979 | Aleev et al. |
| 5,823,190 A | 10/1998 | Voipio |
| 8,078,281 B2 | 12/2011 | Priori et al. |

*Primary Examiner* — Carl H Layno
*Assistant Examiner* — Paula J Stice
(74) *Attorney, Agent, or Firm* — Melvin K. Silverman

(57) ABSTRACT

A apparatus for the electro-physiologic stimulation of the human nervous system includes an electrical assembly having an integrated circuit (IC) producing a sequence of physiologically compatible electromagnetic waveforms, the IC having ungrounded positive and negative outputs of the waveforms, a battery in electrical communication with the IC board, a positive electrode pad in electrical communication with positive outputs of the waveforms, a lower housing in which the IC battery and positive electrode pad are secured, and an upper housing in press-swivel contact with an outer periphery of the lower housing in which 360 degrees of rotation of the upper housing relative to the lower housing is enabled. Also included is a flexible housing for an electrical cable in electrical communication with an opposite end of the cable, carrying the negative sides of the waveforms, and a negative electrode pad in electrical communication with the conductive plate.

12 Claims, 6 Drawing Sheets

US 8,688,240 B1

DEVICE FOR NEURO-PHYSIOLOGIC STIMULATION

REFERENCE TO RELATED APPLICATION

This is a continuation in Parts of U.S. Pat. No. 8,457,754, entitled Method, System and Apparatus for Control of Pancreatic Beta Cell Function to Improve Glucose Homeostatis and Insulin Production, filed Oct. 30, 2012, and the same is incorporated herein by reference in its entirety.

BACKGROUND OF THE INVENTION

With the exception of TENS machines, there exist very few bioelectrical systems that apply an electrical waveform, or a sequence thereof, to the human body. Yet less common are bioelectric systems that apply electrical waveforms to the human neurologic system. Some such systems are implanted into the human body, such as heart pacemakers.

U.S. Pat. No. 8,078,281 to Priori teaches a system of monitoring brain waves and providing a feedback for bio-stimulation of the brain.

U.S. Pat. No. 4,165,750 to Aleev teaches a system of electrical stimulation of muscles.

Electro-stimulation is sometimes used in diagnostic devices as in U.S. Pat. No. 5,823,190 to Voipio which is used in certain examinations of the human eye.

The present invention relates to a special-purpose applicator of electrical waveforms to directly nerves of the parasympathetic nervous system.

SUMMARY OF THE INVENTION

A apparatus for the electro-physiologic stimulation of the human nervous system, comprising a positive electrical assembly having (i) an integrated circuit (IC) producing a sequence of physiologically compatible and acceptable electromagnetic waveforms, the IC having ungrounded positive and negative outputs of the waveforms; (ii) a battery substantially conformal in geometry and in electrical communication with said IC board; (iii) a positive electrode pad in electrical communication with said positive output of said waveforms; (iv) a lower housing in which said IC battery and positive electrode pad are secured; and (v) an upper housing in circumferential press-swivel contact with an outer periphery of said lower housing in which 360 degrees of rotation of said upper housing relative to said lower housing is enabled. The apparatus also includes a flexible housing for said electrical cable. And further includes negative electrical assembly comprising: (i) a conductive plate in electrical communication with an opposite end of said cable, carrying said negative side of said waveforms; (ii) a negative electrode pad in electrical communication with said conductive plate; (iii) a lower housing secured about said conductive plate; and (iv) an upper housing at least partially circumferentially secured about said lower housing, in pressure-swivel relation thereto, said opposite cable end secured between said plate and said upper housing.

It is an object of the invention to provide an apparatus for the application of electro-neurologic waveforms to the anatomy of a patient.

It is a further object to provide an applicator for electro-neurologic waveforms to areas related to the vagus and celiac schema of the sympathetic nervous system.

It is another objet to provide an apparatus useful in innervating neural pathways associated with the pancreas and the activity of its beta cells.

The above and yet other objects of the invention will become apparent from the hereinafter set forth Brief Description of the Drawings, Detailed Description of the invention and Claims appended herewith.

DETAILED DESCRIPTION OF THE INVENTION

Figure 1:
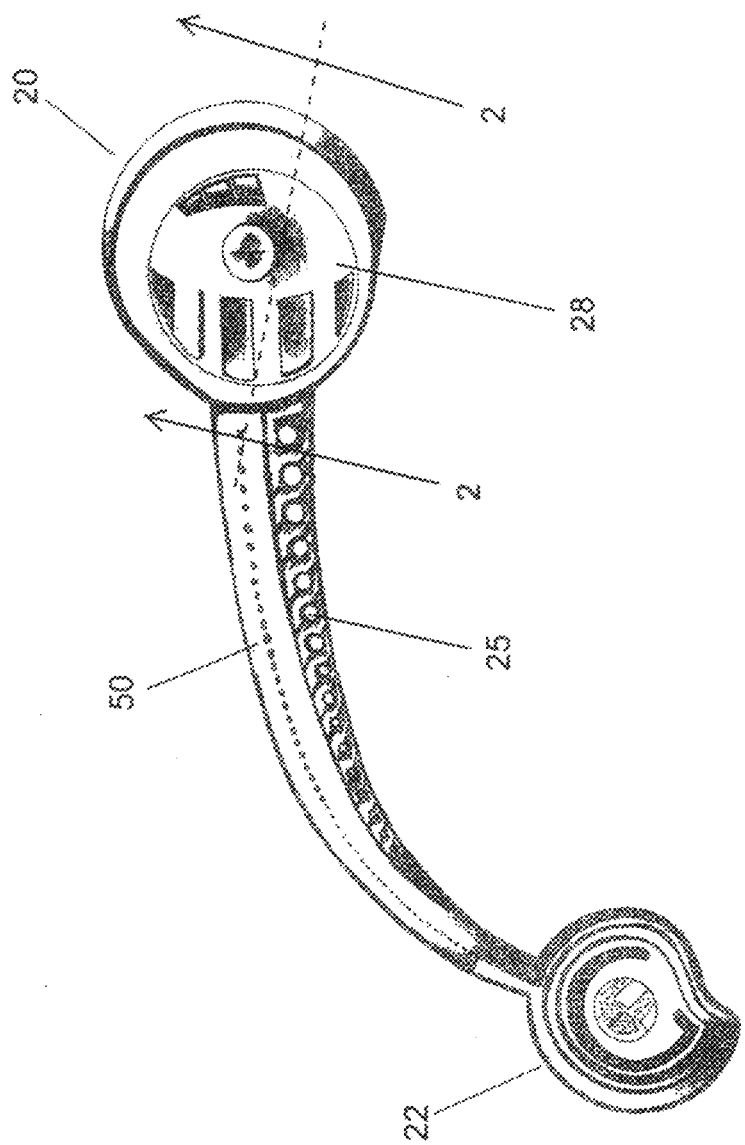
FIG. 1 is a perspective view of the present apparatus.

With reference to FIG. 1 there is shown, in perspective view, the instant device for application of a neurophysiologic electrical waveforms to the human body. A positive electrode assembly 20 and negative electrode assembly 22, connected by a flexible elongate cable housing 50 are shown in a generally top perspective view.

Figure 2:
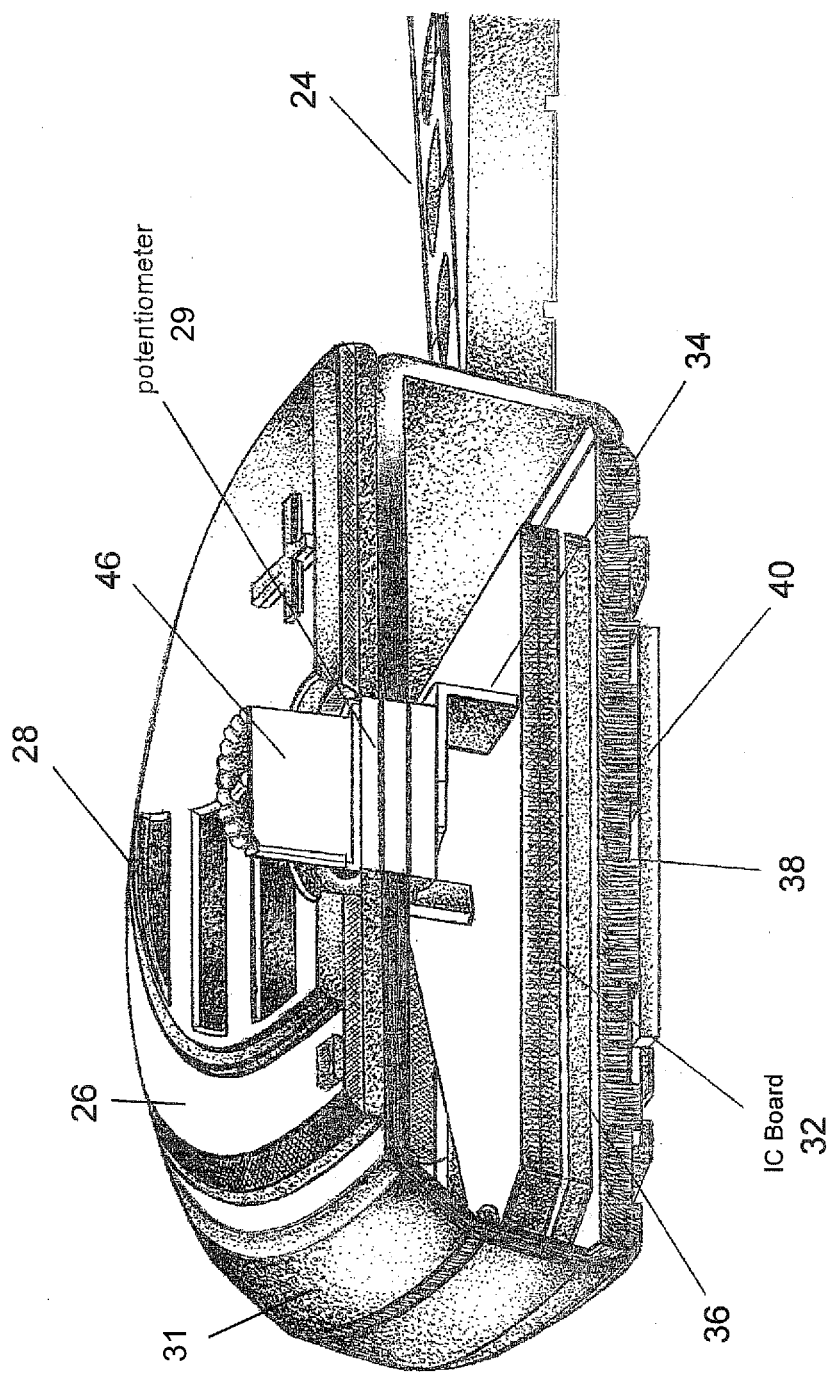
FIG. 2 is a cross-section view of the positive electrode assembly taken along Line 2-2 of FIG. 1.

A cross-sectional view, taken through the middle of positive electrode assembly, through Line 2-2 of FIG. 1 is shown in FIG. 2. Therein may be seen the general top of outer housing 26 of the structure, which centrally disposed therein is on-off switch 46 which also rotates to control potentiometer 29 which controls the voltage amplitude of the waveform applied through the electrodes. Said housing 26 includes vents 28 and employs generally circular sidewalls 31. Potentiometer 29 is offset from integrated circuit ("IC") board 32 through the use of a conductive bracket 34 which electrically communicates with the positive side of the waveform output of circuit (IC) board 32 and stabilizes it relative to battery 36 (which may be a 3 VDC lithium battery) and a flexible biocompatible surface 38, such as a gel, by which metallic electrode 40 comes into contact with the skin of the patient to be treated. IC board 32 is more fully described in parent application Ser. No. 13/663,658, now U.S. Pat. No. 8,457,745, at Cols. 15-17, and FIGS. 13-15 thereof, which has been incorporated hereinto by reference. Further shown in FIG. 2 is a flexible cable 24 (within housing 50) which is in electrical communication with the negative side of the waveform produced by the IC board 32.

Figure 3:
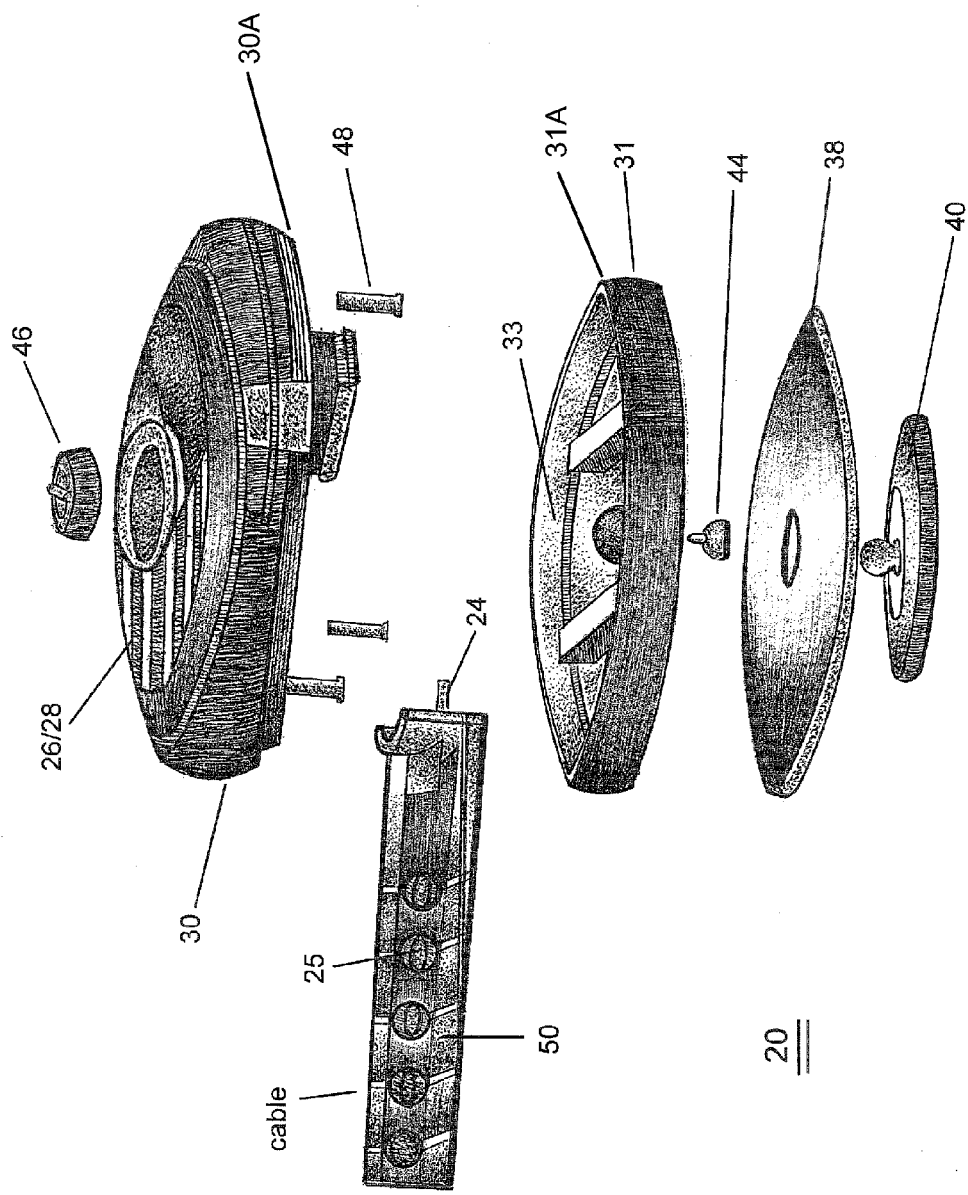
FIG. 3 is an exploded view showing the parts of the positive electrode assembly.

FIG. 3 is an exploded view of FIG. 2 in which, however, cable 24 is shown to the left. As may be noted, the top surface of housing 26 and the electrode 40 at the bottom of each electrode assembly 20 is held together by the metallic electrode 40 and a screw 44 fitting into a knob 45 which communicates with control switch 46. See FIG. 2. Also shown in FIG. 3 are appropriate screws 48 provided to secure the IC board and battery, above-described, and fit within sidewalls 31 of a lower area 33 of the assembly 20, and to secure cable 24 to the IC board 32. Also shown in FIG. 3 is biocompatible surface 38.

It is noted that threads 31A of sidewalls 31 are slidably inserted and press-swivel rotatable upon threaded surface 30A of upper sidewalls 30 of positive electrode assembly 20.

Figure 4:
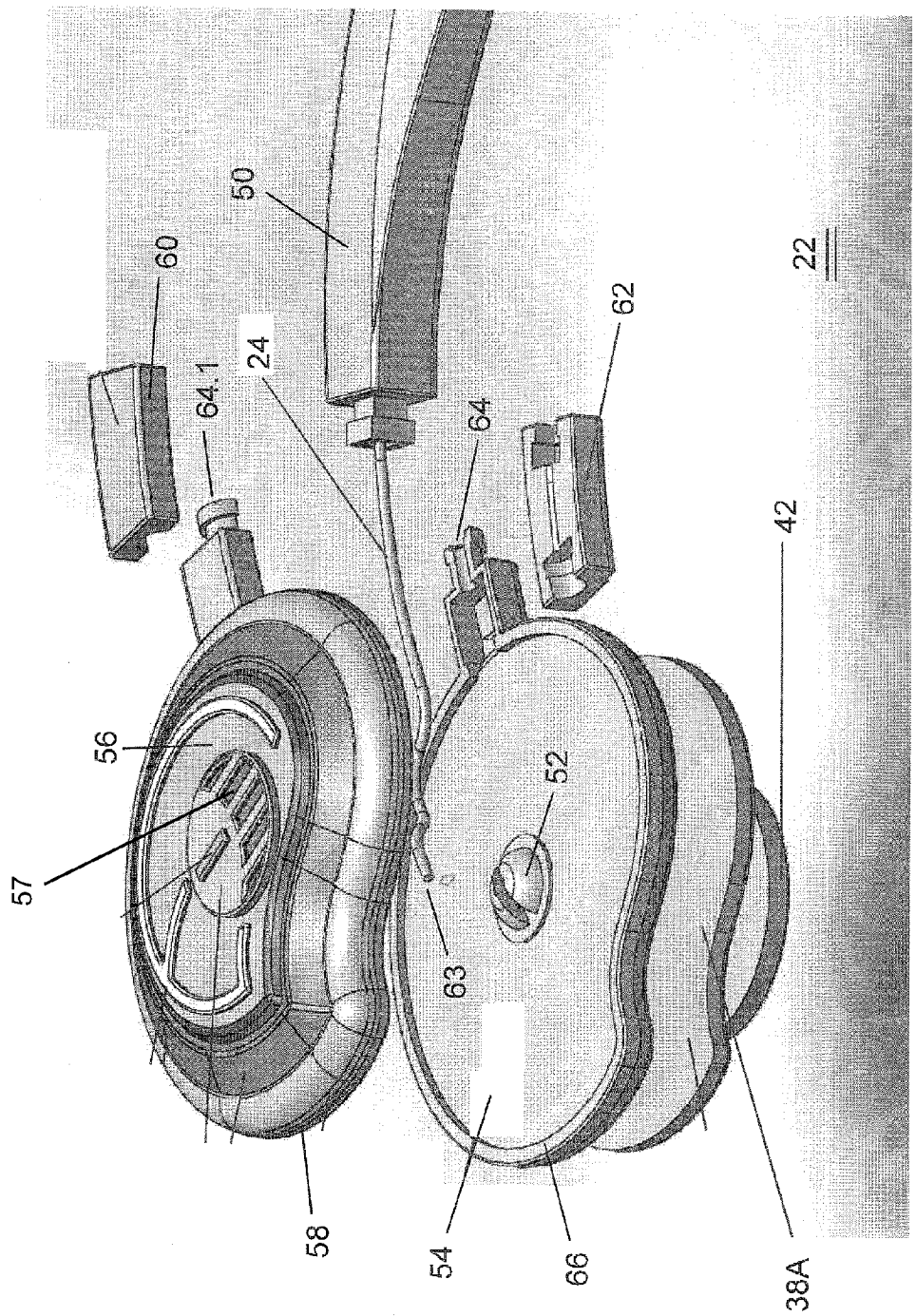
FIG. 4 is an exploded view showing the parts of the negative electrode assembly.

In FIG. 4 is shown an exploded view of negative assembly 22 in which may also been seen cable 24 within cable housing 50. An end 63 of cable 24 is held by axial element 52 and by the walls of assembly 22. Negative electrode assembly 22, like the positive assembly 20, is provided with a metallic electrode 42 and also a layer of electrically conductive gel 38A, above which is provided a plastic plate 54, conformal in geometry to the interior of top region 56 of the negative assembly 22 and sidewalls 58 thereof. Also shown in FIG. 4 are air vents 57. It is also noted that plate 54 provides an insulation between gel 38A and current that passes through wire 24 from the IC board and through axial element 52 to negative electrode 42.

Further provided are protectors 60 and 62 for the exposed segment of cable 24 and, also, to ensure the stability of the cable within entry port 64/64.1, the lower part of which projects from sidewalls 66 and the upper second part of which depends from sidewalls 58 of the negative assembly 22. It is noted that the interface between essentially circular sidewall 58 of the top region 56 and lower sidewalls 66 is such that a limited degree of pressure-swivel polar rotation of the top region relative to the bottom part of assembly 22 can be accomplished. That is, the top relative to the top and sidewalls 56/58 of the negative electrode are able to rotate to a limited extent relative to each other.

It is noted that the same, but to a greater extent, is the case (see FIG. 3) in the relationship of the sidewall of wall 30 of the positive electrode assembly which enables its circular relation to sidewalls 31. As such, negative assembly 22 (see FIG. 1) is able to rotate fully about positive assembly 20, and positive assembly itself is partially rotatable on it own axis. This, as will be seen below, is necessary for the clinical use of the present apparatus.

Figure 5:
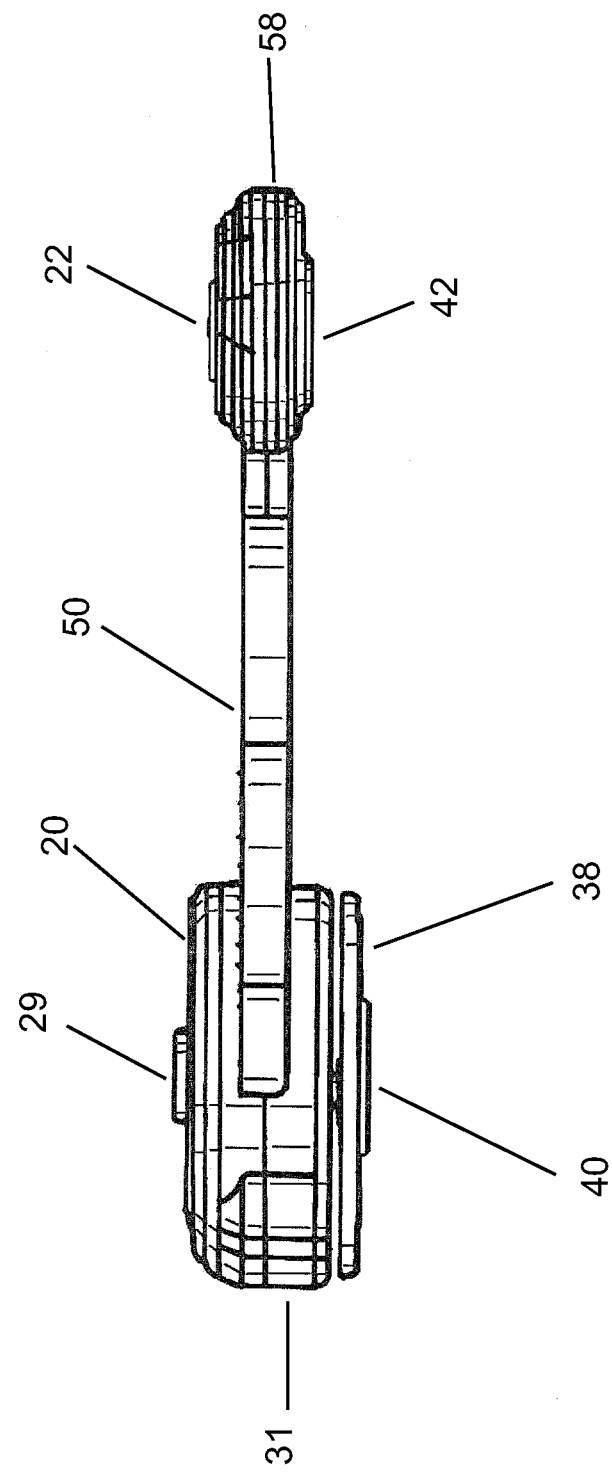
FIG. 5 is a side elevational view of the inventive apparatus.

FIG. 5 is an assembly side view of the entire apparatus above-described.

It should be noted in FIG. 1 that cable 24 is provided with air vents 25 in order to minimize the accumulation of heat within the housing 50 thereof. This is shown in greater detail in FIG. 3.

Figure 6:
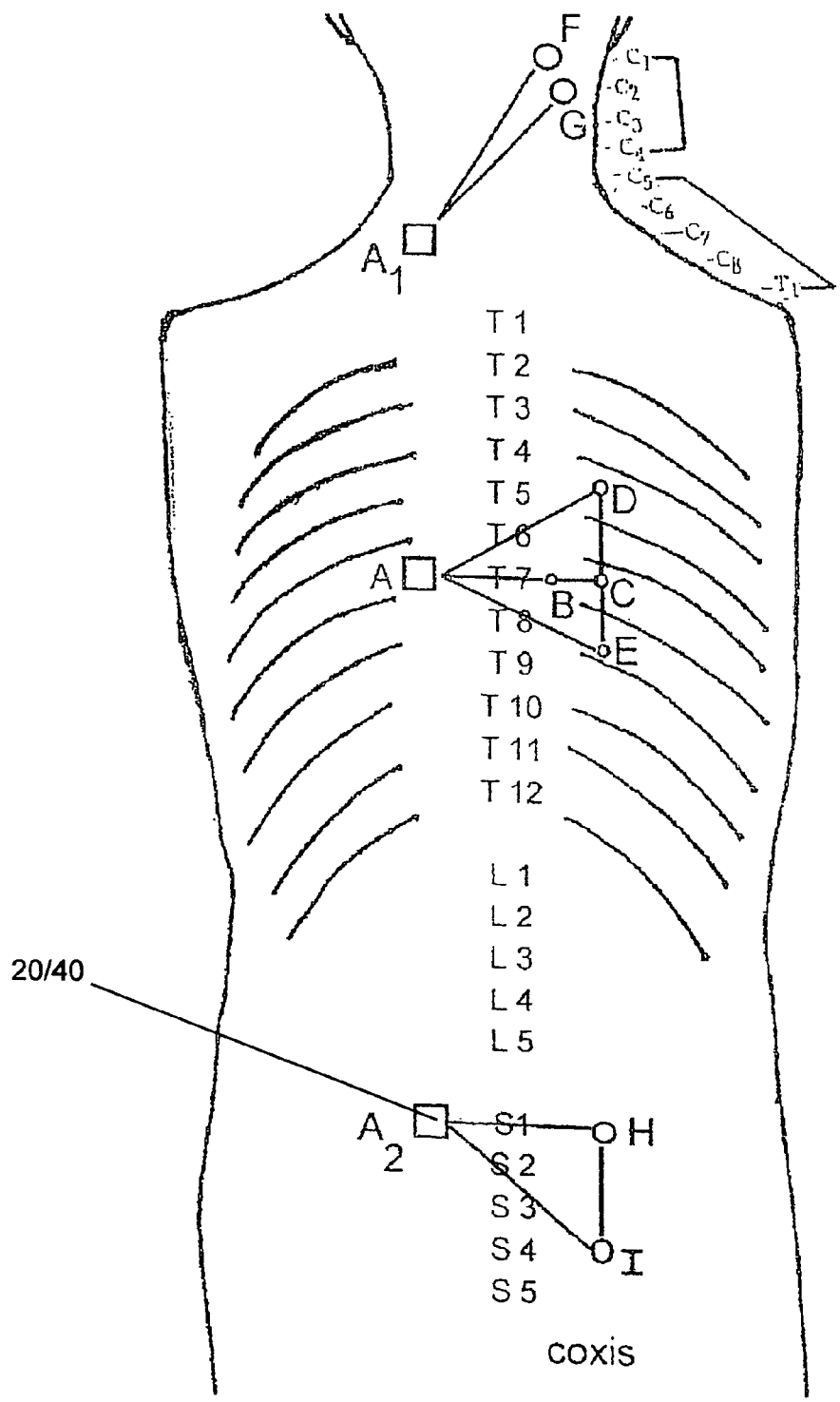
FIG. 6 is a neurological schema of the back showing areas of application of electrodes of the present apparatus.

In FIG. 6 are shown locations at which the electromagnetic physiologic waveform applicator is applied to the human body. Therein, each of the locations indicated at A, A1 and A2 represent locations of positive assembly 20, while the locations indicated by the letters D thru A, F, G, H and I are all locations at which the negative assembly 22 are placed, all in the manner set forth in our parent application Ser. No. 13/663,658, referenced above. Actual contact with the skin occurs via gel through anode electrode 40 and cathode electrode 42. As in noted in said parent application, one-half of the treatment by the respective anodes and cathodes occurs in the manner shown in FIG. 6, whereas in a second phase thereof, the locations of the anode are respectively reversed such that anodes therein are used at the right side of the body and all cathodes are used at the left side. The duration of the on and off periods of the waveform are controlled by a microprocessor in the IC board 32.

While there has been shown and described above the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

The invention claimed is:

1. A apparatus for the electro-physiologic stimulation of the human nervous system, the apparatus comprising:
   (a) a positive electrical assembly comprising;
      (i) an integrated circuit (IC) board producing a sequence of physiologically acceptable electromagnetic waveforms;
      (ii) a battery substantially conformal in geometry and in electrical communication with said IC board;
      (iii) a positive electrode pad in electrical communication with said positive output of said waveforms;
      (iv) a lower housing in which said IC, battery and positive electrode pad are secured; and
      (v) an upper housing in circumferential press-swivel contact with an outer periphery of said lower housing in which 360 degrees of rotation of said upper housing relative to said lower housing is enabled;
      (vi) a first side of an electrical cable in electrical communication with said positive electrode pad;
   (b) a housing for said electrical cable; and
   (c) a negative electrical assembly comprising:
      (i) a conductive element in electrical communication with a second end of said electrical cable, carrying said negative side of said waveforms;
      (ii) a negative electrode pad in electrical communication with said conductive element;
      (iii) a lower housing secured about said conductive element; and
      (iv) an upper housing at least partially circumferentially secured about said lower housing in pressure-swivel relation thereto.

2. The apparatus as recited in claim 1, in which said cable communicates with an electrically negative output of said IC.

3. The apparatus as recited in claim 2, in which a positive output of said IC defines a direct connection to said positive electrode pad.

4. The apparatus as recited in claim 3, in which said housing of said cable comprises a flexible housing.

5. The apparatus as recited in claim 4, in which said housing includes air vents.

6. The apparatus as recited in claim 3, in which a layer of electrically conductive biocompatible material is provided above each of said positive and negative electrode pads.

7. The apparatus as recited in claim 3, in which a potentiometer is provided on said positive electrode to control an amplitude of said waveform output of said IC.

8. The apparatus as recited in claim 7, comprises:
   said potentiometer axially centered at a top of said upper housing of said positive electrode assembly.

9. The apparatus as recited in claim 6, in which said biocompatible material comprises a gel.

10. The apparatus as recited in claim 1, in which each of said upper housings include air vents.

11. The apparatus as recited in claim 10, in which said housing of said cable is provided with air vents.

12. The apparatus as recited in claim 1, in which said IC includes a microprocessor that includes on-off durations of said waveforms.

\* \* \* \* \*